Figure 1:
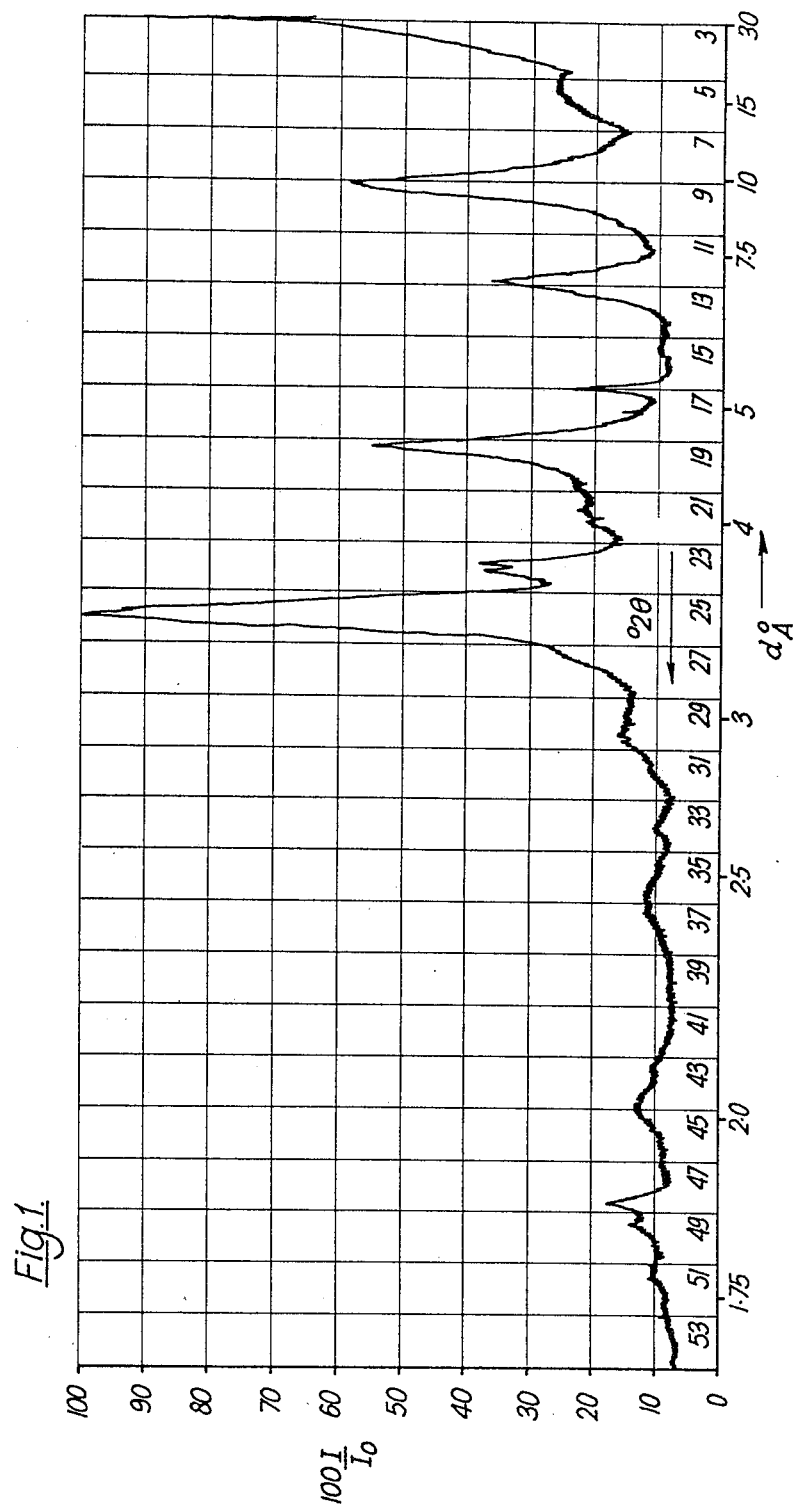

United States Patent [19]
Whittam

[11] 4,300,013
[45] Nov. 10, 1981

[54] ISOMERIZATION OF XYLENES

[75] Inventor: Thomas V. Whittam, Stockton-on-Tees, England

[73] Assignee: Imperial Chemical Industries Limited, London, England

[21] Appl. No.: 158,807

[22] Filed: Jun. 12, 1980

Related U.S. Application Data

[62] Division of Ser. No. 845,391, Oct. 25, 1977, Pat. No. 4,209,498.

[30] Foreign Application Priority Data

Nov. 5, 1976 [GB] United Kingdom ............... 46130/76
Jul. 6, 1977 [GB] United Kingdom ............... 28267/77

[51] Int. Cl.$^3$ .................... C10G 11/05; C07C 5/27; C07C 15/8
[52] U.S. Cl. .................... 585/481; 208/120; 208/DIG. 2; 252/455 Z; 252/466 J; 585/470; 585/487; 585/940
[58] Field of Search ......................... 585/481

[56] References Cited

U.S. PATENT DOCUMENTS

| | | | |
|---|---|---|---|
| 3,849,463 | 11/1974 | Dwyer et al. | 423/328 |
| 4,021,502 | 3/1977 | Plank et al. | 585/533 |
| 4,052,479 | 10/1977 | Chang et al. | 585/640 |
| 4,060,590 | 11/1977 | Whittam et al. | 423/328 |
| 4,066,714 | 1/1978 | Rodewald | 585/640 |
| 4,162,214 | 7/1979 | Maslyanski et al. | 585/471 |

*Primary Examiner*—Delbert E. Gantz
*Assistant Examiner*—G. E. Schmitkons
*Attorney, Agent, or Firm*—Cushman, Darby & Cushman

[57] ABSTRACT

A silica-containing material related to zeolites and referred to hereinafter as FU-1 has the composition 0.6 to 1.4 $R_2O.Al_2O_3$.over 5 $SiO_2$.0 to 40 $H_2O$, (where R is a monovalent cation or 1/n of a cation of valency n) and is characterized inter alia by its X-ray diffraction pattern. It can be made by hydrothermal synthesis in presence of methylated quaternary onium compounds. It is useful as a catalyst for hydrocarbon conversion reactions, especially isomerization of xylenes.

5 Claims, 2 Drawing Figures

ISOMERIZATION OF XYLENES

This is a division of application Ser. No. 845,391 filed Oct. 25, 1977 now U.S. Pat. No. 4,209,498.

This invention relates to a silica-containing material having at least the properties of cation exchange and selective adsorption in common with zeolites and to derivatives thereof, to a method of making such materials and to processes using them. The material will be referred to hereinafter as "zeolite FU-1" or simply "FU-1". These materials, method and processes are the subject of provisional specifications accompanying UK patent applications Nos. 41630/76 and 28267/77, which specifications are incorporated herein by reference.

FU-1, like zeolite nu-1 described in our co-pending UK application Nos. 40631/75—4957/76—31641/76, to which corresponds published Netherlands specification 7610766, can be made by reaction of a silica source and an alumina source in the presence of methylated quaternary ammonium compounds and/or methylated quaternary phosphonium compounds in suitable conditions of mixture molar composition, temperature and time, which conditions in part border on those for making nu-1 so that it is possible to make each with the other as an impurity.

A considerable number of zeolite preparations involving the tetramethylammonium cation has already been described. These have been surveyed up to the end of 1972 by D. W. Breck in "Zeolite Molecular Sieves" (Wiley-Interscience 1974) pages 304–312, 348–378. The following is a list of what are believed to be the most pertinent examples, with references, of those disclosed up to September 1977:

| | |
|---|---|
| N - A, N - X, N - Y | US 3306922; J. Chem. Soc. 1961, 971; |
| N | US 3414602; J. Chem. Soc. Dalton 1972, 2534-; |
| ZK-4 | UK 1026879; Inorg. Chem. 1966, 5 1537-; |
| alpha | UK 1074130 (US 3375205) |
| ZSM-4 | UK 1117568, 1227294, 1297256, 1321460 and 1365318 |
| omega | UK 1178186 |
| TMA - offretite | UK 1188043 |
| Ag-2 | UK 1413470 |
| FW | Canadian 996536 (US Serial No. 684482 of Nov. 1967) |
| Phi | German OS 2513682 (US Serial No. 456803 of 1 April 1974). |
| TMA - Na - E | J. Chem. Soc. A 1970, 1470-1475 at 1474 |
| nu-1 | UK application 40631/75-4957/76 - 31641/76, published as Netherlands application 7610766 |

According to the invention a silica-containing material, referred to hereinafter as FU-1, has the chemical composition 0.6 to $1.4R_2O.Al_2O_3$.over $5SiO_2.0$ to $40H_2O$ where R is a monovalent cation or (1/n) of a cation of valency n and $H_2O$ is water of hydration additional to water notionally present when R is H, and has an X-ray diffraction pattern substantially as set out in Table 1 below.

TABLE 1

| d (A) | 100 I/Io | d (A) | 100 I/Io |
|---|---|---|---|
| 9.51 | 31 | 4.48 | 6 |
| 8.35 | 8 | 4.35 | 13 |
| 6.92 | 28 | 4.07 | 19 |
| 6.61 | 9 | 400 | 9.4 |
| 6.26 | 9 | 3.89 | 13 |
| 5.25 | 16 | 3.73 | 28 |
| 4.61 | 63 | 3.68 | 3 |
| | | 3.44 | 100 |

These lines were measured on the sodium/tetramethylammonium (TMA) form of FU-1 described in Example 1 below, but we find that the pattern of the hydrogen form, as exemplified by the corresponding material (Example 2) from which all the TMA and all but 300 ppm w/w of $Na_2O$ has been removed differs negligibly from the above pattern. The diffraction peaks observed are very broad suggesting that FU-1, at least as so far produced, occurs in small crystallites typically 100–500 Angstrom units (A) in diameter.

Figure 2:
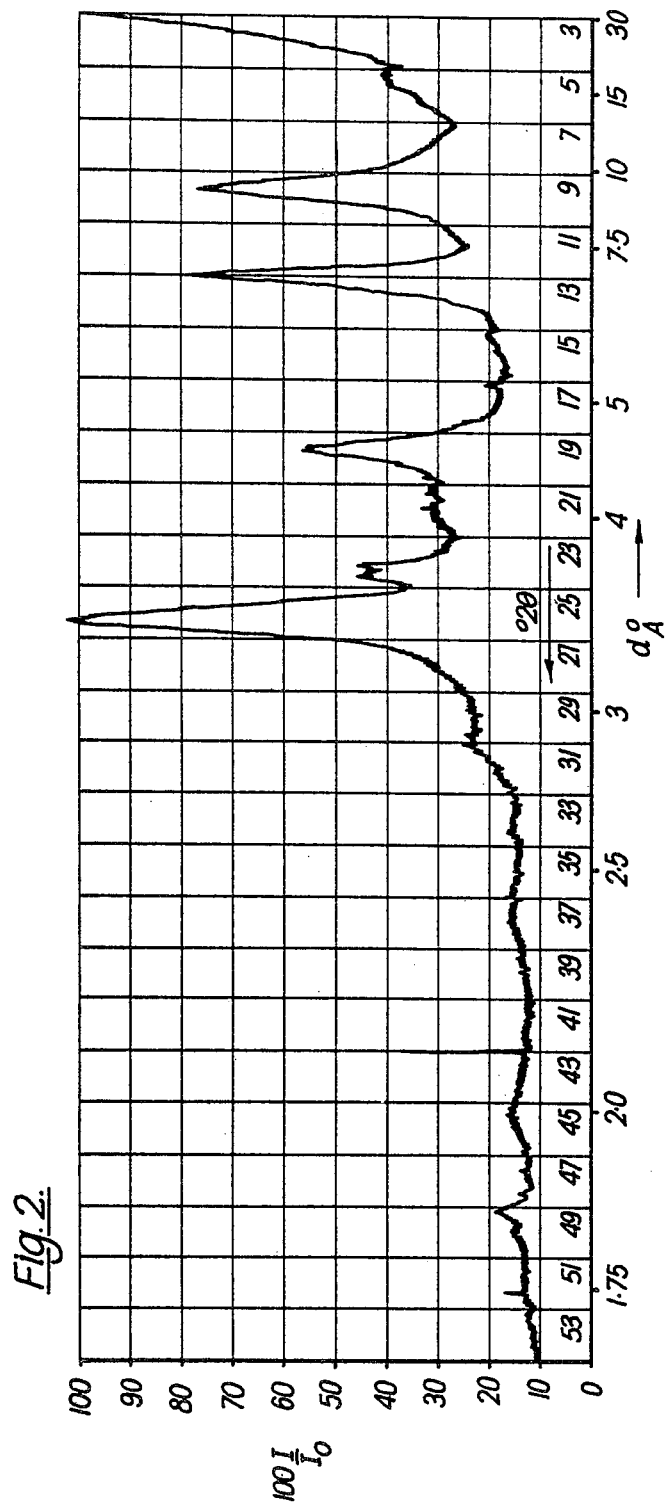

A more detailed X-ray diffraction table is set out below in Example 25 and in the accompanying drawings in which FIG. 1 relates to FU-1 as synthesised and dried, containing sodium oxide and tetramethylammonium (TMA) oxide and decomposition products thereof; and FIG. 2 relates to FU-1 from which sodium and TMA have been removed, that is, in its hydrogen form.

FU-1 has an infra-red spectrum, having some features in common with those of known zeolites. Its clearest absorption peaks are set out in Table 2: these data were determined using the Nujol mull technique for materials described in Example 24.

TABLE 2

| Na, TMA | | H | |
|---|---|---|---|
| frequency $cm^{-1}$ | absorption | frequency $cm^{-1}$ | absorption |
| 1230–1240 | medium | 1230–1240 | medium |
| 1055–1065 | strong | 1070–1080 | strong |
| 950* | weak | 950* | none |
| 780–790 | weak | 800 | weak |
| 590 | weak | 590–600 | weak |
| 430–440 | medium-strong | 440–450 | medium-strong |

*The absorption at 950 $cm^{-1}$ is due to TMA

The crystalline structure of FU-1 as shown by electron microscope examination at magnification up to 500,000 can consist of very thin sheets of angularly interlocking platelets, typically 50 to 400 A thick and agglomerated into packs of total thickness in the range 0.1 to 10 microns.

Within the above definition of chemical composition the number of molecules of $SiO_2$ is more typically at least 10, for example 15–300 and FU-1 appears to be most readily formed in a state of high purity when the number of molecules of $SiO_2$ is in the range 15 to 45, for example 15 to 30. It is believed to be unusual to have "hydrophobic properties" (see below) at such a low $SiO_2$ level. The upper limit for $SiO_2$ that can exist in the FU-1 structure is not yet known.

This definition includes both freshly prepared FU-1 and also forms of it resulting from dehydration and/or calcination and/or ion exchange. In freshly prepared FU-1 the radical R is or includes ammonium or phosphonium selected from methylated quaternary ammonium and methylated quaternary phosphonium and cationic degradation products thereof (referred to hereinafter as Q) and may include an alkali metal, conveniently sodium, to the extent typically of 0.1 to 0.4 mols per $Al_2O_3$. The freshly prepared material often also contains quaternary compound in excess of the 1.4 molecules of $R_2O$ set out in the composition definition, typically in the range 0.5 to 2.5 molecules. If the stoichiometry of FU-1 is the same as that of true zeolites, all this excess $R_2O$ appears to be trapped in the crystal lattice.

The $H_2O$ content of freshly prepared FU-1 depends on the conditions in which it has been dried after synthesis and is typically in the range 1–20 molecules per $Al_2O_3$ when the drying temperature is in the range 70°–140° C.

In calcined forms of FU-1, R may be alkali metal but include less ammonium or phosphonium compound than in freshly made material, since these compounds are removed by calcination, in the presence of air, steam or ammonia, leaving hydrogen as the balancing cation.

Among the ion-exchanged forms of FU-1 the ammonium ($NH_4^+$) is of importance since it can be readily converted to the hydrogen form by calcination. The hydrogen-form and forms containing metals introduced by ion exchange are described further below.

FU-1 has molecular sieve properties analogous to those of known zeolites.

Representative sorption percentages at 25° C., p/po about 0.5, McBain sorption balance, for FU-1 in a variety of forms are given in Table 3. When FU-1 contains more than 0.2% of carbon, which is present as quaternary compounds and their decomposition products, it is "hydrophobic", that is, it adsorbs more n-hexane than water, at least in short sorption times. When it contains under 0.2% of such carbon it sorbs water and n-hexane more nearly equally, but water sorption is still unlike that of many known zeolites, which in the conditions used reach 90% of equilibrium sorption in 10 minutes. The H-RE-FU-1 from Example 24 is, however, more normal in this respect.

Variants of FU-1 of especial interest include the hydrogen form containing less than 4000, especially less than 1000 ppm of alkali metal calculated as equivalent $Na_2O$; and also forms in which the content of quaternary compounds or their decomposition products, expressed as carbon, is in the range 0.05 to 1.0% w/w as results from calcination in air or in less than 0.05% w/w as results from calcination in ammonia.

It thus appears that for the Na/TMA form of FU-1 the n-hexane sorption is in the range 1.5 to 3.0 times the water sorption, and that for suitably prepared H FU-1 this ratio can be 5 to 10. The rare-earth FU-1 and ammonia-calcined FU-1 could evidently be used for separating p-xylene from mixtures with its isomers.

FU-1 is characterised further by its absorption capacity for various dyestuffs. The following is a comparison with known zeolites:

TABLE 3

| Sample | % C | Time, min | water 2.7 | n - hexane 4.3 | triethylamine* 6.9 | p - xylene 5.9 | m - xylene 6.1 |
|---|---|---|---|---|---|---|---|
| Example 1 (uncalcined) | | 120 | 1.7 | 3.7 | NA | 0.3 | NA |
| Example 2 (air-calcined) | 0.3 | 120 | 1.3 | 9.1 | NA | 0.4 | NA |
| | | 1020 | NA | NA | NA | 5.0 | NA |
| Example 22 (air-calcined) | under 0.2 | 5 | 4.4 | 7.6 | 6.3 | 0.7 | NIL |
| | | 120 | 9.4 | 8.0 | 10.0 | 0.7 | 0.1 |
| 23 A (i) (air-calcined) | 0.8 | 10 | 0.4 | 3.2 | 4.2 | 0.2 | NIL |
| | | 60 | 3.7 | 3.4 | 4.7 | 0.8 | 0.1 |
| 23 A (ii) | under 0.2 | 10 | 5.4 | 2.7 | 4.0 | 3.4 | NIL |
| H-RE-FU-1 | | 60 | 6.4 | 4.1 | 5.1 | 4.4 | 0.3 |
| 23 B ($NH_3$ calcined, then air-calcined) | NIL | 10 | 3.7 | 3.3 | 4.3 | 4.4 | NIL |
| | | 60 | 6.5 | 3.7 | 5.0 | 4.5 | 0.4 |
| 24 (air-calcined) | under 0.2 | 10 | 4.0 | 3.1 | 5.1 | 0.3 | NIL |
| | | 60 | 7.0 | 4.4 | 8.0 | 0.4 | 0.4 |

TABLE 4

| | (a) cationic dyes | | | | |
|---|---|---|---|---|---|
| | acriflavine | phenosafranine | carbocyanine | methyl red | toluylene red |
| H FU-1 | nil | very strong | medium | nil | nil |
| H nu-1 | nil | nil | very strong | very strong | nil |
| H ZSM-5 | very strong | very strong | very strong | very strong | very strong |
| H Y | medium | nil | very strong | nil | nil |
| H mordenite | very strong | nil | very strong | nil | nil |

Since it sorbs isobutane readily, to the extent of 4% w/w at 25° C., 760 mm pressure, when in the hydrogen form containing less than 300 ppm of $Na_2O$ and containing 0.3% w/w of carbon after calcination to remove TMA, its entry ports are evidently more than 5.0 A in diameter. Since it sorbs p-xylene slowly, its entry ports are about 6.0 A in diameter. For this purpose and in Table 3 below, the molecular diameter is the "CSA"-diameter, that is, the width of the molecule in the plane in which its cross-sectional area is a minimum. This parameter is discussed in the above-cited "Zeolite Molecular Sieves", page 636. The CSA- diameter of isobutane is 5.0 A and other diameters are given in Table 3.

TABLE 5

| | (b) other dyes | | |
|---|---|---|---|
| | Alizarin | Aurin | aluminon C.1.724. |
| H FU-1 | nil | nil | nil |
| H nu-1 | weak | nil | nil |
| H ZSM-5 | very strong | very strong | very strong |
| H Y | nil | nil | nil |
| H mordenite | medium | very strong | medium |

The invention provides also a method of making FU-1 by reacting an aqueous mixture comprising at least one silica source, at least one alumina source and at least one methylated quaternary ammonium or methylated quaternary phosphonium compound, the mixture having the molar composition

| | |
|---|---|
| $SiO_2/Al_2O_3$ | at least 10, preferably 10 to 200, esp. up to 80 |
| $OH^-/SiO_2$ | 0.2 to 12.0 preferably 0.2 to 0.4, esp. 0.4 to 0.8 |
| $X^-/SiO_2$ | 0 to 3.0 |
| $Q^+/(Q^+ + Ak^+)$ | 0.05 to 1.0, especially 0.2 to 0.9 |
| $OH^-(Ak^+/(Q^{30} + Ak^+))/SiO_2$ | 0 to 0.8, especially 0.1 to 0.5 |
| $H_2O/OH^-$ | 25 to 250, especially 50 to 150 | where $Q^+$ is methylated quaternary ammonium ion or methylated quaternary phosphonium ion:

$Ak^+$ is alkali metal ion; and $X^-$ is a monovalent anion of a strong acid or $(1/n)$ of a strong acid anion of valency n, the conditions being chosen to produce a presipitate containing at least 20% w/w of FU-1.

This definition of the synthesis method is in terms of the ionic theory and takes account of the presence of strong acid anions and of alkali metal and quaternary cations introduced by deliberate addition or formed in situ by adding a strong acid or a strong acid salt of aluminium or Q. When no such anions or cations are present the definition of the method reduces to the form set out in the provisional specification, namely

| | |
|---|---|
| $SiO_2/Al_2O_3$ | at least 10, preferably 10 to 200, esp. up to 80 |
| $Na_2O/SiO_2$ | 0 to 0.4, especially 0.05 to 0.25 |
| $(Ak_2O + Q_2O)/SiO_2$ | 0.1 to 6.0, preferably 0.1 to 2.0, esp. 0.2 to 0.4 |
| $H_2O/(Ak_2O + Q_2O)$ | 50 to 500, especially 100 to 300 |
| $Q_2O/(Na_2O + Q_2O)$ | 0.05 to 1.0, especially 0.2 to 0.9 | where

Q is methylated quaternary ammonium or methylated quaternary phosphonium; and $Ak_2O$ and $Q_2O$ refer to free $Ak_2O$ and $Q_2O$ only, the conditions being chosen so as to produce a precipitate containing at least 20% of FU-1.

The expression "free $Ak_2O$" and "free $Q_2O$" are generally understood in the zeolite art to denote hydroxides or salts of very weak acids such as aluminic or silicic acid such that the $Ak_2O$ and $Q_2O$ are effective in the zeolite synthesis reaction. If waterglass is used as a silica source, the content of free $Ak_2O$ and/or $Q_2O$ can be decreased to within the specified range by adding acid or adding alumina and/or Q in the form of a salt of a strong acid, for example as sulphate, nitrate or halids. When non-free $Ak_2O$ and/or $Q_2O$ are present, the relative proportions of free $Ak_2O$ and free $Q_2O$ are assumed to be the same as the relative proportions of the total content of Ak ions and Q ions.

The above-defined broadest conditions are numerically similar to thus specified for making zeolite nu-1, but within these ranges the formation of FU-1 is favoured by the following conditions:

(a) limited silica to alumina ratio in the synthesis mixture, especially to up to 80, for example to the range 20 to 60;

(b) relatively low values of the ratio $Q^+/(Ak^+ + Q^+)$, for example in the range 0.2 to 0.4;

(c) agitation at relatively high rates, depending on the value of ratio (b). For example when ratio (b) is 0.3 the peripheral velocity of a rotating blade in the mixture is preferably at least 60 cm sec$^{-1}$ and when ratio (b) is 0.9 the velocity is preferably at least 120 cm sec$^{-1}$. These velocities apply to a blade 25 mm in diameter moving with a clearance of 25 mm from other solid members and would naturally be different for larger scale operations. The agitation should preferably be such as to keep the whole mixture well mixed, rather than merely to apply shear to small volume-elements successively.

(d) relatively high water content and little, if any, solvent other than water;

(e) seeding with FU-1 or with zeolite nu-1; possibly other silica-containing materials may be suitable as seeds, and the results obtained using highly dispersed solid silica such aerosil or rubber-reinforcing grade precipitated silica suggests that the silica itself may provide nuclei for the growth of the FU-1 lattice. The proportion of seed is suitably in the range 5–15% w/w of the silica in the silica source, but smaller quantities, for example down to about 1% or even 0.2%, appear to have a useful effect.

These conditions may be summarised as providing for a high rate of renewal of the supply of soluble species at the surface of a solid reactant. For example the formation of FU-1 may depend on the attack by alkali metal and silicate ions on a silico-aluminate precipitate formed at an early stage in the synthesis, so that in conditions of strong agitation silica is leached out of the precipitate thus lowering its silica content into the range typical of FU-1, whereas in conditions of weak agitation such silica leaching soon ceases in the absence of renewed supplies of alkali metal and silicate ions, thus permitting the high-silica precipitate to crystallise with little if any loss of silica. Another possible mechanism is that formation of FU-1 requires a high rate of supply of aluminate ions at the sites where they are being absorbed into a silica-containing lattice to give FU-1 in the early stages of the reaction, whether that lattice belongs to the silica source or to FU-1 or to seed zeolite. The invention is, of course, not declared to be limited to this mechanism. Some of the combinations of conditions known to produce FU-1 at various levels or purity, including substantially 100%, are described in the Examples.

In preparations outside the condition described in the Examples it is advisable to check by sampling and X-ray examination that FU-1 is formed in an adequate state of purity in line with control procedures commonly used in zeolite preparation as a result of the metastable nature of zeolites.

The silica source may be any of those commonly considered for use in synthesising zeolites, for example powdered solid silica, silicic acid, colloidal silica or dissolved silica. Among the preferred silicas usable are precipitated silicas, especially those made by precipitation from an alkali metal silicate solution, such as the type known as "KS 300" made by AKZO, and similar products, aerosil silicas, fume silicas and silica gels suitably in grades for use as reinforcing pigments for rubber or silicone rubber. Colloidal silicas of various particle sizes may be used, for example 10–15 or 40–50 microns, as sold under the Registered Trade Marks "LUDOX", "NALCOAG" and "SYTON". The usable dissolved silicas include commercially available waterglass silicates containing 0.5 to 6.0, especially 2.0 to 4.0 mols of $SiO_2$ per mol of $Na_2O$ or $K_2O$ "active" alkali metal silicates as defined in UK Pat. No. 1,193,254, and silicates made by dissolving silica in alkali metal or quaternary ammonium hydroxide as a preliminary stage in making the synthesis mixture. A mixture of silicate sources can be used.

The alumina source is most conveniently an alkali metal aluminate, but can be or include an aluminium salt for example the chloride, nitrate or sulphate or alumina itself, which should preferably be in a hydrated or hydratable form such as colloidal alumina, pseudo-böhmite, böhmite, gamma alumina or the alpha or beta trihydrate.

Part or all of the alumina can be provided by an aluminosilicate compound, suitably to the extent of at least 20%, especially 50 to 100% w/w of the alumina source. This does not include any alumino-silicate added as seed. If the aluminsilicate compound contains sufficient silica, it can provide the whole of the silica source. However, since the silica to alumina ratio of FU-1 is higher than that of readily available aluminosilicate compounds, the reaction mixture will normally contain a further silica source. Such an aluminosilicate compound can be synthetic or naturally-occurring. If it is synthetic it can for example be a crystalline compound, such as a suitable zeolite or an amorphous compound such as a gel or a zeolite precursor or a silica/alumina cracking catalyst. If it is naturally-occurring it may be for example a clay such as kaolin (especially in the form known as metakaolin made by calcination of kaolin at 500°–950° C., especially 530°–600° C.), or one or more of attapulgite, dickite, halloysite, illite or montmorillonite. A naturally-occurring zeolite may be used if desired. Substances such as nepheline and kalsilite, which are available naturally or synthetically, can be used. In assembling the reaction mixture, account should be taken of other reactants introduced as part of the aluminosilicate material, such as water and alkali metal compounds; and preferably any interfering constituents should be substantially absent. The aluminosilicate compound used can be one that has been made by treating with acid or with non-interfering cations the corresponding compound containing interfering cations. If desired, the aluminosilicate can have been de-aluminised by acid or chromium leaching. If the aluminosilicate is introduced in shaped form, synthesis conditions can be chosen to produce FU-1 in shaped form, thus making agglomeration steps unnecessary.

The radical Q is preferably tetramethylammonium.

The water content of the reaction mixture is preferably over 500, especially in the range 1000–5000, mols per mol of $Al_2O_3$.

The reaction should be continued preferably up to the time at which the solid phase contains not less than 50% w/w of FU-1. A typical time is in the range 12–300 hours. The temperature is suitably in the range 80°–250° C. and in otherwise comparable conditions appears to be desirably lower than when making zeolite nu-1.

When no seed is present the temperature is preferably in the range 150°–230° C., in order to obtain adequately pure FU-1 within a convenient time. When, however, seed is present, temperatures in the range 90°–200° C. can be used and are preferred. At the end of the reaction period the solid phase is collected on a filter and washed and is then ready for further steps such as drying, dehydration ion-exchange and removal of carbon compounds.

If the product of synthesis is to be calcined at any stage, the preferred calcination temperature is in the range 350°–500° C. When oxygen is present care is taken to prevent overheating. Calcination conditions are chosen to effect the required extent of carbon removal, as explained above. If the product of synthesis contains alkali metal ions, these have to be at least partly removed in order to prepare the hydrogen form of FU-1 and this can be done by ion exchange with an acid, especially a strong mineral acid such as hydrochloric acid or by way of the ammonium compound, made by ion exchange with a solution of an ammonium salt such as ammonium chloride. Such ion exchange can be carried out by slurring once or several times with the solution. The zeolite is usually calcined after ion exchange and may be calcined before or between stages. Preferably at least half the alkali metal ions are replaced by hydrogen or ammonium. FU-1 containing not more than 4000 ppm w/w of alkali metal and preferably not more than 1000 ppm, calculated as equivalent $Na_2O$, is very useful as an acid catalyst or as a support for a hydrogenation/dehydrogenation catalyst.

In general, the cation(s) of zeolite FU-1 can be replaced by any cation(s) of metals, and particularly by those in Groups IA, IB, IIA, IIB, III (including rare earths), VIIA (including manganese), VIII (including noble metals) and by lead and bismuth. The Periodic Table is as in "Abridgments of Specifications" published by the U.K. Patent Office.

In order to prepare a catalyst, FU-1 can be incorporated in an inorganic matrix, with other materials which can be either inert or catalytically active. The matrix may be present simply as a binding agent to hold the small zeolite particles (0.1 to 10 microns) together, or it may be added as a diluent to control the amount of conversion in a process which may otherwise proceed at too high a rate, leading to catalyst fouling as a result of excessive coke formation. Typical inorganic diluents include catalyst support materials such as alumina, silica and kaolinic clays, bentonites, montmorillonites, sepiolite, attapulgite, Fullers earth, synthetic porous materials such as $SiO_2$—$Al_2O_3$, $SiO_2$—$ZrO_2$, $SiO_2$—$ThO_2$, $SiO_2$—$BeO$, $SiO_2$—$TiO_2$, or any combination of these oxides. An effective way of mixing zeolite FU-1 with such diluents is to mix appropriate aqueous slurries in a mixing nozzle and then to spray-dry the slurry. Other ways of mixing can be used. Treatments such as ion exchange and carbon compounds removal can be carried out before, during or after matrix formation or at more than one stage.

If FU-1 in any cationic form or as a catalytic composite is exchanged or impregnated with hydrogenation/dehydrogenation components, such as Ni, Co, Pt, Pd, Re, Ph, hydrocracking and reforming catalysts can be made, especially if the $Ak_2O$ content is not more than 0.03% w/w as equivalent $Na_2O$.

The invention provides a process of hydrocarbon conversion in the presence of a catalyst containing FU-1, which is active in hydrocarbon reactions such as those cracking and/or isomerisation reactions catalysed by acids. The cracking process is especially applicable to heavy feedstocks containing more than 10 carbon atoms in the molecule and the products of cracking include an unusually high proportion of hydrocarbons under $C_6$.

Among the isomerisation reactions is the equilibration of xylene mixtures, especially as a stage in the production of para-xylene. Thus according to the invention a hydrocarbon conversion process comprises contacting an alkylbenzene or a mixture of alkylbenzenes under isomerisation conditions in the vapour or liquid phase with a catalyst comprising FU-1.

In the vapour phase suitable isomerisation conditions include a temperature in the range 100°–600° C., preferably 200°–450° C. and a pressure in the range 0.5–50, preferably 1–5, atm abs. These conditions are used preferably in the absence of added free hydrogen and with FU-1 containing no hydrogenation/dehydrogenation component.

In the liquid phase suitable isomerisation conditions include a temperature in the range 0°–350° C., a pressure in the range 1–200, preferably 5–70 atm abs., and, in a flow system, a weight hourly space velocity (WHSV) in the range 1–100, preferably 1–30, the higher flow rates being used at the higher temperatures. Optionally a diluent is present, suitably one or more of those having a critical temperature higher than the isomerisation temperature being used and including toluene, trimethylbenzene, naphthenes and paraffins. Preferably the diluent if present amounts to 1–90% w/w of the feed to the isomerisation reaction. In this liquid phase process the catalyst also preferably contains no hydrogenation/dehydrogenation component and no added free hydrogen is present.

Optionally isomerisation in the vapour phase is conducted in the presence of hydrogen. A suitable mole ratio of hydrogen to alkylbenzene lies in the range 3 to 30:1. If hydrogen is used, the catalyst should comprise a hydrogenation/dehydrogenation component, preferably a metal of Group VIII of the Periodic Table, especially platinum. The amount of metal preferably lies in the range 0.1 to 2% w/w on the total catalyst. If desired, the catalyst may contain one or more additional metals, for example rhenium, suitably in the range 0.1 to 2% w/w on the total catalyst.

Preferably the alkylbenzene is a xylene, for example m-xylene for conversion to p-xylene, or a mixture of xylenes, possibly with ethylbenzene. The amount of ethylbenzene present will depend to some extent on the source of the xylene mixture but will usually lie in the range 0 to 25% w/w, especially 6 to 25% w/w of the feedstock, since the process is able to handle feeds containing relatively high amounts of ethylbenzene.

The isomerisation may be carried out in the presence of water vapour in a concentration of, for example 500 to 10,000 and preferably 1000 to 5000 ppm w/w of the feedstock.

In a preferred form, the isomerisation process is effected in the presence of a $C_{2-10}$ alkane and/or alicyclic hydrocarbon in a concentration of 0.5 to 20, especially 1.5 to 12% of the feedstock suitably in the absence of hydrogen, the catalyst containing no hydrogenating component, by which is meant a component which would hydrogenate the alkyl benzene to the corresponding naphthene under the conditions of the reaction if hydrogen were present.

Suitable alicyclic hydrocarbons include octahydroanthracenes, tetralin, decalin, cyclohexane, cyclo-octane and cyclohexyl cyclohexane, as well as their alkyl, especially $C_1$ to $C_4$ alkyl, substituted derivatives, for example mono, di-, tri- and tetra-methyl cyclohexanes, ethyl cyclohexane, ethylmethyl and diethyl-cyclohexanes. Suitable alkanes include especially those having at least one secondary or tertiary hydrocarbon atom, for example isobutane, isopentane or isohexane.

In any hydrocarbon conversion process according to the invention the contents of alkali metal, quaternary ion and trapped quaternary compound are subject to optimisation for the particular process to be operated. The above-mentioned preferred forms of FU-1 in which at least 50% of the alkali metal ions are replaced by hydrogen or ammonium, and especially forms containing not more than 4000 ppm w/w of alkali metal calculated as $Na_2O$, are of wide applicability however. Smaller contents of alkali metal, for example up to 1000 and especially up to 300 ppm w/w as equivalent $Na_2O$, are preferred in FU-1 to be used for catalysing xylenes isomerisation. It appears to be unnecessary to have present ions other than hydrogen and (for hydroisomerisation) Group VIII metal ions. The FU-1 suitably contains onium compounds and their decomposition products to the extent of 0.05 to 1.0% w/w, such as are present after substantial removal of such materials by calcination in air, when it is to be used in xylenes isomerisation.

The catalyst containing FU-1 slowly becomes covered with carbon during hydrocarbon conversion. It can be regenerated by burning off the carbon, suitably by means of a nitrogen-air mixture containing 3–6% w/w of oxygen. A suitable temperature is in the range 400°–500° C., and oxidation should usually be continued until the outlet gas contains under 500 ppm v/v of carbon dioxide.

In the Examples the composition of the synthesis mixtures was calculated on the basis of the following ingredient specifications, in which percentages are by weight:

TABLE 6

|  | Formula | Molecular weight |
|---|---|---|
| Sodium aluminate | 1.25 $Na_2O \cdot Al_2O_3$ | 143.6 per free $Na_2O$ |
|  |  | 179.4 per $Al_2O_3$ |
| Aluminum sulphate | $Al_2(SO_4)_3 \cdot 16H_2O$ | 630.4 per $Al_2O_3$ |
|  |  | 105.1 per $X^-$ |
|  |  | 39.4 per $H_2O$ |
| Silica KS300 - | various batches, composition quoted in Examples. | |
| Silica Aerosil 300 | $SiO_2$ 99.8% under 0.02% $Al_2O_3$ and $Na_2O$ | 60 |
| Sodium metasilicate pentahydrate | $Na_2SiO_3 \cdot 5H_2O$ | 212.05 per $SiO_2$ or free $Na_2O$ |

TABLE 6-continued

| | Formula | Molecular weight |
|---|---|---|
| | | 42.4 per $H_2O$ |
| Water-glass | $Na_2O . 3.4SiO_2 .$ | 698.2 per free $Na_2O$ |
| | $24H_2O$ | 205.4 per $SiO_2$ |
| | | 38.8 per $H_2O$ |
| Sodium hydroxide | NaOH | 80 per free $Na_2O$ |
| Sodium sulphate | $Na_2SO_4$ | 71.03 per $X^-$ |
| Tetramethylammonium hydroxide TMAOH (under 50 ppm $Na_2O$) | $(CH_3)_4NOH$ 25% $H_2O$ 75% | 182 per $Q_2O$ 18 |
| TMACl | $(CH_3)_4NCl$ | 219 per $Q_2O$; 109.5 per $X^-$ |
| Sulphuric acid | $H_2SO_4$ 98% $H_2O$ 2% | 50 per $X^-$ 900 per $H_2O$ added 50 per $H_2O$ (by neutralisation) |

Notes:
1. Seed was not counted as an ingredient and is indicated by an asterisk in the Tables below.
2. "Free $Na_2O$" means $Na_2O$ added as hydroxide, aluminate or silicate and is taken as equal to half the number of OH ions.
3. Washing water was demineralised.
The following other general notes apply to the Examples:
1. In each preparation the mixture was thoroughly stirred at room temperature before heating it to synthesis temperature;
2. Percentages and ppm are by weight unless otherwise stated;
3. Process space velocities are expressed as GHSV(volumes of gas per unit volume of zeolite per hour) or WHSV (weight of feed per unit weight of catalyst-filled space per hour).
4. X-ray diffraction patterns were determined by means of Cu K alpha radiation in a Philips vertical diffractometer.
5. "Pyrex" is a Registered Trade Mark in UK.

EXAMPLE 1

Preparation of Na-TMA-FU-1

The reaction mixture had the composition:
12.64 $Na_2O.5.4(TMA)_2O.Al_2O_3.59.3SiO_2.3586$ $H_2O$
Solid silica (56.6 g of KS300, batch, A, 98.9% $SiO_2$, 1.1% $Na_2O$) was suspended in a mixture of 61.6 g of TMAOH solution in 700 g of water. Sodium aluminate (2.8 g) and sodium hydroxide (13.5 g) were dissolved in 100 g of water and the resulting solution stirred into the silica suspension over 10 minutes. The total mixture was heated at 180° C. with reciprocatory agitation in a stainless steel 1 liter autoclave under 20 atm. pressure of nitrogen for 6 days. The solid phase was collected on a filter, washed, and then dried overnight at 120° C. giving a product of composition:

0.33$Na_3O$.1.3$(TMA)_2O.Al_2O_3.22SiO_2.5H_2O$ of which about 0.6 mol of $(TMA)_2O$ may be non-structural. Its X-ray diffraction pattern had the peaks set out in Table 1 above. The peaks are broad and typical of an ill-defined crystalline product, but the major constituent is evidently a material not previously known, that is, FU-1. From the breadth of the peak at 5.25 A the mean crystallite size appeared to be about 400 A, and from the breadth at 4.61 A about 150 A.

The material was examined by electron microscopy at a magnification of 50000 and observed to be in the form of very thin, probably crumpled, sheets agglomerated into particles 0.1 to 10 microns in diameter. (In later examination of FU-1 samples at higher magnification the crumpled sheet structure appears to be due to anqularly interlocking platelets).

Sorption data determinations are described in Example 2 below.

EXAMPLE 2

Preparation of hydrogen form of FU-1 and determination of sorptive properties

A sample of the product of Example 1 was heated slowly to 450° C., controlling the rate of heating to avoid any temperature runaway due to burn-off of TMA, then calcined overnight at 450° C. in a stream of air saturated with water at 25° C. It was then cooled and refluxed for 5 hours with 2 ml of 5% HCl in water per g of FU-1, filtered and washed with demineralised water. The washed product was re-slurried with 60 ml of 3.65% HCl in water, stirred for 1 hour at 50° C., washed and dried. The dried product, the hydrogen form of FU-1, contained 0.3% of carbon and 300 ppm of $Na_2O$ and had an X-ray diffraction negligibly different from that of the product of Example 1.

Samples of the dried product were allowed to come to equilibrium in presence of the vapours of (separately) water, n-hexane, isobutane and p-xylene. The results are shown in Table 3 above.

EXAMPLE 3

Use of FU-1 in hydrocarbon cracking

A sample of hydrogen FU-1 from Example 2 was charged to a "pulse" reactor and heated to 450° C. in a nitrogen (14 psig) flow of about 3 l/hr. Then pulses of n-hexadecane vapour were fed into the gas current and the mixture leaving the FU-1 analysed by gas liquid chromatography. The conversion of hexadecane was 80%. Similar comparative runs were carried out using zeolites HZSM-5, H nu-1, and REY and a silica/alumina cracking catalyst. The product distributions are set out in Table 7.

TABLE 7

| Catalyst | Percentage $^w/w$ Product Distribution, carbon numbers | | | |
|---|---|---|---|---|
| | under 6 | 6–7 | 7–10 | 11–15 |
| FU-1 | 82 | 9 | 9 | nil |
| H ZSM-5 | 51 | 8 | 34 | 7 |
| H nu-1 | 64 | 17 | 13 | 6 |
| REY | 51 | 28 | 13 | 7 |
| $SiO_2/Al_2O_3$ | 65 | 15 | 12 | 8 |

FU-1 is therefore of potential value when products in the LPG range are required, and the low proportion of $C_6$ to $C_{15}$ products suggests that its aromatisation tendency may be low. The products of the FU-1 cracking contained both straight and branched-chain hydrocarbons.

EXAMPLE 4

Unseeded preparation in low silica to alumina ratio mixture (a) The reaction mixture had the composition:

3.16Na$_2$O.1.5Q$_2$O.Al$_2$O$_3$.14.5SiO$_2$.900H$_2$O

Solid silica KS300A (49.1 g) was dispersed in 275 g water and into the dispersion was stirred a solution made by dissolving TMAOH solution (59.5 g) and sodium hydroxide (1.7 g) in water and then adding sodium aluminate (9.8 g) to it. The mixture was reacted in a 1 liter "Pyrex" liner in a 5 liter autoclave quiescently under 80 atm pressure of nitrogen at 180° C. for 3 days. The solid phase was collected on a filter, washed and dried overnight at 180° C. It has the composition:

0.82Na$_2$O.1.07Q$_2$O.Al$_2$O$_3$.24SiO$_2$.2H$_2$O, of which about 0.9 molecules of Q$_2$O may be non-structural. Its X-ray diffraction pattern was substantially the same as that shown in Table 1 above, with no detectable impurities. As in Example 1, at the low value of Q/(Q+Na) used agitation need not be vigorous.

(b) A similar run was carried out using 675 mols of water per Al$_2$O$_3$ instead of 900. The product was zeolite nu-1. This result is consistent with the hypothesis that aluminate ions were less readily available than in (a) owing to the higher viscosity.

EXAMPLE 5

Preparation of mixture of FU-1 and TMA-sodalite

Example 1 was repeated except that the water content of the mixture was 2600 mols per mol of Al$_2$O$_3$ instead of 3000 and the synthesis time was 3 days instead of 6. The product consisted of 80% FU-1 and B 20% TMA-sodalite.

EXAMPLE 6

Seeded preparation of near-pure FU-1 in a stainless steel reactor at higher temperatures A mixture having the composition:

12.64Na$_2$O.5.4Q$_2$O.Al$_2$O$_3$.59.3SiO$_2$.4140H$_2$O, the silica being KS300A, and containing in addition a trace of nu-1 zeolite as seed (about 0.5% on the silica) was reacted in a stainless steel autoclave 75% v/v full without agitation and without inert gas under pressure at 220° C. for 24 hours. The solid phase was collected on a filter, washed, dried at 120° C. and examined by X-ray diffraction. It consisted of FU-1 with a trace of nu-1.

EXAMPLE 7

Seeded preparation of FU-1/nu-1 mixture

The mixture 12.64Na$_2$O.5.4(TMA)$_2$O.Al$_2$O$_3$.59.3SiO$_2$.3000H$_2$O was prepared as in Example 1 on the scale of 1.75 g of sodium aluminate and seeded with low D-spacing zeolite nu-1 at 7% on the silica in the mixture. It was reacted in a 1 liter "Pyrex" liner in a 5 liter autoclave under 20 atm nitrogen pressure and without agitation at 175° C. for 3 days. The product was collected on a filter, washed, and dried overnight at 80° C. Its X-ray diffraction pattern showed that FU-1 and nu-1 were present in the approximate proportion 75:25 w/w. Its composition was:

0.2Na$_2$O.1.3(TMA)$_2$O.Al$_2$O$_3$.40SiO$_2$.5H$_2$O

EXAMPLE 8

Unseeded larger scale preparation of substantially pure FU-1

The mixture 12.64Na$_2$O.5.4(TMA)$_2$O.Al$_2$O$_3$.59.3SiO$_2$.3586H$_2$O was prepared as in Example 1 on the scale of 30.6 g of sodium aluminate and reacted in a 25 liter stainless steel autoclave with reciprocatory agitation and without pressurised inert gas at 170° C. for 24 hours. The solid phase was collected on a filter, washed and dried at 80° C. for 24 hours. Its X-ray diffraction pattern showed that it contained FU-1 without detectable impurity. Its chemical composition was:

0.11Na$_2$O.1.07Q$_2$O.Al$_2$O$_3$.20SiO$_2$.3586H$_2$O

EXAMPLE 9

Effect of type of agitation, unseeded

Three samples of a mixture of composition 9.64Na$_2$O.5.4Q$_2$O.Al$_2$O$_3$.59.3SiO$_2$.3008H$_2$O, in which the silica was KS300A, were made up on the scale of 2.7 g of sodium aluminate and reacted by the following procedures:

(a) in a 1 liter "Pyrex" liner in a 5 liter autoclave under 20 atm nitrogen pressure at 180° C. for 5 days, without agitation;

(b) as (a) but with agitation by rocking;

(c) in a 1 liter stainless steel autoclave without inert gas and with moderate agitation (900 rpm) at 180° C. for 2 days.

Each solid phase formed was collected on a filter, washed, dried at 120° C. overnight and examined by X-ray diffraction and by chemical analysis. The results were as follows:

TABLE 8

| Pro-ducts | Phases by X ray diffraction | Composition by moles | | | | |
|---|---|---|---|---|---|---|
| | | Na$_2$O | Q$_2$O | Al$_2$O$_3$ | SiO$_2$ | H$_2$O |
| a | Zeolite nu-1, low d type as major phase. | 0.3 | 2.2 | 1 | 55 | 6 |
| b | nu-1 medium d type + cristobalite. | 0.1 | 1.5 | 1 | 63 | 4 |
| c | FU-1 with trace of zeolite nu-1. | 0.3 | 1.5 | 1 | 25 | 5 |

Evidently agitation favours formation of FU-1. (Runs a and b are not according to the invention).

EXAMPLE 10

Effect of rate of mixing, unseeded

Three samples of a mixture of composition 1.89Na$_2$O.13.75Q$_2$O.Al$_2$O$_3$.59.3SiO$_2$.1930H$_2$O, in which the silica was KS300A, were made up on the scale of 3.3 g of sodium aluminate and reacted without pressurised inert gas in a 1-liter stainless steel autoclave at 170° C. for 24 hours, each with agitation by a paddle at a different rate. The paddle blade edge rotated at 25 mm from the autoclave wall. Each resulting solid phase was collected on a filter, washed, dried at 120° C. overnight and examined by X-ray diffraction. The results are shown in Table 9.

TABLE 9

| Paddle speed rpm | Phase present | Product molar composition | | | | |
|---|---|---|---|---|---|---|
| | | $Na_2O$ | $Q_2O$ | $Al_2O_3$ | $SiO_2$ | $H_2O$ |
| a 150 | nu-1 split peak type (maj) | 0.1 | 2.7 | 1 | 68 | 7 |
| b 900 | FU-1 minor, some nu-1 | 0.4 | 1.5 | 1 | 33 | 4 |
| c 1800 | FU-1 substantial, nu-1 minor | 0.1 | 1.3 | 1 | 28 | 5 |

Thus, although the sodium content of the mixture was low in proportion to the Q content, rapid agitation has moved the product composition away from nu-1 and towards FU-1.

EXAMPLE 11

Effect of temperature, unseeded

Three samples of the mixture used in Example 1 were reacted without pressurised gas each at a different temperature, all with agitation at 900 rpm. The solid phase was collected on a filter, washed, dried at 120° C. overnight and examined by X-ray diffraction. The results are shown in Table 10.

TABLE 10

| Temp °C. and time | Phase present | Product molar composition | | | | |
|---|---|---|---|---|---|---|
| | | $Na_2O$ | $Q_2O$ | $Al_2O_3$ | $SiO_2$ | $H_2O$ |
| a 180, 6 days | major phase FU-1, no detectable impurities | 0.35 | 1.3 | 1 | 25 | 7 |
| b 130, 3 days | major phase ZSM-4, no detectable impurities | 0.8 | 0.2 | 1 | 12 | 10 |
| c 110, 5 days | major phase TMA-analycite, no detectable impurities | 0.8 | 0.2 | 1 | 8 | less than 1 |

EXAMPLE 12

Seeded preparations using different silica source

The reaction mixture had the composition 3.75Na<sub>2</sub>O.8.4Q<sub>2</sub>O.Al<sub>2</sub>O<sub>3</sub>.52.7SiO<sub>2</sub>.2195H<sub>2</sub>O, and was made up by suspending solid silica (60 g Degussa Aerosil 300) in a mixture of TMAOH solution (117 g) and water (660 g) and adding sodium hydroxide (3.8 g) sodium aluminate (3.4 g); then 6 g of FU-1 from the preparation described in Example 8 were stirred in as seed. The mixture was reacted in a 1 liter stainless steel autoclave without agitation and without pressurised inert gas at 175° C. for 7 days. The solid phase was recovered as in Example 1. Its composition was 0.2Na<sub>2</sub>O.1.3Q<sub>2</sub>O.Al<sub>2</sub>O<sub>3</sub>.26SiO<sub>2</sub>.5H<sub>2</sub>O.

Its content of $Q_2O$ over the normal level in a zeolite was less than in the previous Examples. Its X-ray diffraction pattern showed FU-1 to be the major product, with no other phase detected.

EXAMPLE 13

Preparation of H-FU-1

A sample of the product of Example 8 was, without calcination, ion-exchanged as described in Example 2, washed and dried, and then calcined in air for 17 hours at 450° C. The calcined product had the composition 0.01Na<sub>2</sub>O.Al<sub>2</sub>O<sub>3</sub>.22.5SiO<sub>2</sub> and contained 0.2% of organic material calculated as carbon.

EXAMPLE 14

Hydrocarbon treatment processes using undiluted H-FU-1 from Example 13

The procedure described in Example 3 was applied to 1-methylnaphthalene, tetralin and decalin (a cis-trans 52:48 mixture). The product distribution is shown in Table 11, in comparison with those obtained in like tests of zeolites REY (5% in inert silica) and HZSM-5 undiluted. It is evident that FU-1 is highly active for these reactions. Using the methylnaphthalene feed it was more active than either prior zeolite and gave a higher yield of products in the naphtha range. Using tetralin FU-1 gave a significantly higher yield of C<sub>11+</sub> products of lower boiling point. Using decalin FU-1 cracked the cis isomer preferentially, unlike ZSM-5 and produced substantially more product at C<sub>7</sub> and below.

EXAMPLE 15

Xylenes isomerisation using FU-1/alumina (corrected)

FU-1 prepared as in Example 1 and then ion-exchanged and calcined to give the hydrogen form containing 400 ppm of Na<sub>2</sub>O and 0.7% of carbon was formed into catalyst pellets containing 67% FU-1 and the balance gamma alumina. A sample (8.8 g) of the pellets was placed in a laboratory size reactor and a vaporous feed of mixed xylenes passed over then at 450° C., 1 atm pressure in a series of three runs at rates in the range 49–60 ml h<sup>−1</sup> (WHSV 4.8 to 5.9).

TABLE 11

| Feed | 1 - methylnaphthalene | | | Tetralin | | | Decalin | | |
|---|---|---|---|---|---|---|---|---|---|
| Catalyst | FU-1 | REY | H ZSM-5 | FU-1 | REY | H ZSM-5 | FU-1 | REY | H ZSM-5 |
| Products % | | | | | | | | | |
| Under C<sub>6</sub> | 1.5 | 0.5 | 1.2 | 14.8 | 2.3 | 17.5 | 30.3 | 8.3 | 25.8 |
| C<sub>6</sub> + C<sub>7</sub> | 1.8 | 1.2 | 1.3 | 17.8 | 4.5 | 28.0 | 16.4 | 10.0 | 6.8 |
| C<sub>8</sub>–C<sub>10</sub> | 7.1 | 2.9 | 3.3 | 18.3 | 7.0 | 35.6 | 24.8 | 23.4 | 26.8 |
| C<sub>11</sub> boiling below feed. | 21.6 | 14.2 | 22.0 | 14.4 | 15.6 | 3.0 | NA | NA | NA |
| C<sub>11</sub> boiling above | 23.4 | 16.3 | 16.0 | 10.1 | 8.6 | 11.0 | NA | NA | NA |

TABLE 11-continued

| Feed | 1 - methylnaphthalene | | | Tetralin | | | Decalin | | |
|---|---|---|---|---|---|---|---|---|---|
| Catalyst | FU-1 | REY | H ZSM-5 | FU-1 | REY | H ZSM-5 | FU-1 | REY | H ZSM-5 |
| feed. Conversion (%) | 55.5 | 35.1 | 43.8 | 75.4 | 38.0 | 86.2 | cis 85 trans 58 | 52 30 | 59 60 |

The percentage composition of the feed and products are summarised in Table 12.

TABLE 12

| | FEED | RUN 1 | RUN 2 | RUN 3 |
|---|---|---|---|---|
| Benzene | 0.06 | 0.32 | 0.26 | 0.27 |
| Toluene | 1.98 | 3.12 | 2.95 | 3.10 |
| Ethylbenzene | 6.92 | 6.47 | 6.60 | 6.62 |
| Para-xylene | 8.72 | 18.12 | 17.1 | 17.9 |
| Meta-xylene | 55.6 | 48.2 | 48.6 | 48.1 |
| Ortho-xylene | 26.1 | 23.1 | 23.8 | 23.4 |
| n-nonane | 0.69 | 0.65 | 0.65 | 0.65 |

EXAMPLE 16

Xylenes isomerisation using undiluted FU-1

A batch of FU-1 was prepared by heating together silica (138 g), sodium aluminate (6.9 g), TMAOH solution (150.4 g) and water (2350 g) at 175° C. for 48 hours with stirring at 150 rpm. (The mixture has the composition $$3.8Na^+ . 5.4Q^+ . 9.14OH^- . Al_2O_3 . 59.0SiO_2 . 3555 H_2O).$$

The reacted mixture was then cooled, discharged from the reactor and filtered. It was activated by washing with hydrochloric acid and then calcined in air for 450° C. for 16 hours. A sample was pelleted without added alumina or other diluent. Over a charge of 250 g of the pellets there was passed at 450° C., 10 psig pressure a feed of mixed xylenes containing 8.65% para-xylene and 47.14% meta-xylene in the vapour phase for 72 hours. Table 13 shows the para-xylene content of the product and the Selectivity Factor (Sf) at various times where

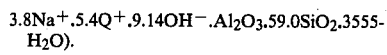

$$Sf = \frac{\text{Rate of Disproportionation of xylenes}}{\text{Rate of Isomerisation of xylenes}}$$

TABLE 13

| TIME ON STREAM, h | PARA-XYLENE IN PRODUCT, % | Sf |
|---|---|---|
| 9 | 15.56 | 0.26 |
| 12 | 16.16 | 0.22 |
| 18 | 16.20 | 0.20 |
| 24 | 16.02 | 0.16 |
| 30 | 16.58 | 0.18 |
| 36 | 16.30 | 0.14 |
| 42 | 16.89 | 0.15 |
| 48 | 16.66 | 0.17 |
| 54 | 15.94 | 0.16 |
| 60 | 16.20 | 0.16 |
| 66 | 16.32 | 0.18 |
| 72 | 16.13 | 0.18 |

EXAMPLE 17

Example 16 was repeated with addition to the feed of 5% cyclohexane. The results are summarised in Table 14.

TABLE 14

| TIME ON STREAM, h | PARA-XYLENE IN PRODUCT, % | Sf |
|---|---|---|
| 3 | 16.91 | 0.28 |
| 6 | 16.79 | 0.25 |
| 9 | 16.76 | 0.21 |
| 12 | 16.54 | 0.21 |
| 18 | 15.84 | 0.19 |
| 24 | 16.28 | 0.19 |
| 30 | 15.98 | 0.18 |
| 36 | 15.78 | 0.15 |
| 42 | 15.52 | 0.18 |
| 48 | 16.04 | 0.18 |
| 54 | 15.78 | 0.17 |
| 60 | 15.83 | 0.13 |
| 66 | 15.64 | 0.14 |
| 72 | 15.59 | 0.13 |

Examples 15-17 clearly show the enhanced para-xylene content of the product compared with that of the feedstock. We have found that the FU-1 catalyst is several times more active than conventional silica-alumina. Loss of xylenes by disproportionation over both FU-1 catalyst and conventional catalyst appears to be similar initially but as time on-line increases the loss of xylenes over FU-1 is less than that over the conventional catalyst.

EXAMPLE 18

Isomerisation in presence of steam

To a raw vaporised xylenes stream containing 8.7% of p-xylene, 9.2% of ethylbenzene and balance o-xylene and m-xylene was added 4.25% v/v of steam (7500 ppm). The mixture was passed at WHSV 5.2 h$^{-1}$ over a 100 g charge of pelleted FU-1 as described in Example 23 A(i) below. The temperature was 450° C. and pressure 10 psig. A similar run was carried out without added steam. The p-xylene and ethylbenzene percentages in the product at intervals are shown in Table 15.

TABLE 15

| | p - xylene | | ethylbenzene | |
|---|---|---|---|---|
| Time h | with steam | without steam | with steam | without steam |
| 3 | 16.6 | 16.8 | 8.1 | 8.3 |
| 6 | 16.8 | 16.6 | 8.2 | 8.5 |
| 9 | 16.6 | 16.1 | 8.4 | 8.6 |
| 12 | 16.4 | 16.3 | 8.4 | 8.5 |
| 18 | 16.0 | 15.9 | 8.5 | 8.6 |
| 24 | 15.6 | 15.6 | 8.6 | 8.7 |

It is evident that the conversion of ethylbenzene is increased without effect on the production of p-xylene.

EXAMPLE 19

Preparation using waterglass and aluminium sulphate (a) A synthesis mixture having the composition 35.43Na$^+$.10.8Q$^+$.Al$_2$O$_3$.60.24SiO$_2$.17.-49OH$^-$.28.74X$^-$.1689.6H$_2$O was made up by mixing 100 g TMAOH solution and 314 g of waterglass with 75 g of water, stirring in a solution of 16 g of aluminium sulphate and 28.9 g of sulphuric acid in 408 g of water, and then stirring in 10 g of a sample of zeolite nu-1 of the high d-spacing type in the form of very small crystallites, containing about 2.4 mols of (TMA)$_2$O per mol of Al$_2$O$_3$. The mixture was transferred to a 1 liter stainless steel autoclave and with stirring at 1800 rpm reacted at 180° C. for 24 hours under autogenous pressure, then cooled. The solid was collected on a filter, washed thoroughly with water and dried overnight at 80° C. The dried solid had an X-ray diffraction pattern showing it to contain FU-1 as its major constituent.

(b) The procedure of run (a) was repeated with the exception that the seed was zeolite FU-1 containing 2.1 mols of Q$_2$O per Al$_2$O$_3$ instead of nu-1 and the stirrer rate was also lower (450 rpm). The product consisted of nu-1 and FU-1 approximately equal quantities, according to its X-ray diffraction pattern.

(c) The procedure of run (a) was repeated with quantities adjusted to give a synthesis mixture having the composition 14.6Na$^+$.3.0Q$^+$.8.6OH$^-$.9.0X$^-$.Al$_2$O$_3$.25SiO$_2$.901.5H$_2$O.

The seed was FU-1 from Example 24 (a) below: 4 g of seed was used in a mixture on the scale of 236 g waterglass (101.2 g of SiO$_2$). The synthesis time was 12 hours at 180° C., in a stainless steel autoclave stirred at 400 rpm. The product contained FU-1 as its major constituent, with a trace of TMA-sodalite.

EXAMPLE 20

Effect of seeding on synthesis temperature

The synthesis procedure was repeated using a KS-300A mixture having the composition 12.6Na$_2$O.5.4Q$_2$O.Al$_2$O$_3$.59.3SiO$_2$.2700H$_2$O in a variety of conditions of scale, agitation temperature and of presence or absence of seed. In each seeded preparation the seed was the product of run a and had the composition 0.3Na$_2$O.1.1(TMA)$_2$O.Al$_2$O$_3$.20SiO$_2$.4.5H$_2$O having been dried at 100° C. before analysis and use. The seed in runs b-f was taken from the same batch and that marked with an asterisk in run h was a sample of a larger repeat batch. It was also noted that the FU-1 produced in run d had a higher silica to alumina ratio than the seed, namely 0.38Na$_2$O.0.87(TMA)$_2$O.Al$_2$O$_3$.29SiO$_2$.7H$_2$O.

The results are shown in Table 16. It is evident that, provided a seed is present, the synthesis leads to FU-1 despite the low temperature. These results are to be compared with those set forth in Example 11.

TABLE 16

| Run No. | Scale, g Na AlO$_2$ | seed, g per g SiO$_2$ | Agit., rpm | Vessel material | Temp, °C. | Time, h | Product, according to X-ray diffraction |
|---|---|---|---|---|---|---|---|
| a | 2.6 | none | 150 | SS | 180 | 17 | FU-1 major constituent. |
| b | 0.052 | 0.1 FU-1 | No | SS | 130 | 72 | FU-1 major constituent. |
| c | 0.052 | 0.1 FU-1 | No | SS | 130 | 120 | About 20% FU-1, rest amorphous. |
|   |   |   |   |   |   | 240 | FU-1 major constituent. |
| d | 1.4 | 0.1 FU-1 | 200 | "Pyrex" | 95 | 192 | Medium FU-1, major constituent amorphous. |
|   |   |   |   |   |   | 264 | FU-1 medium to major constituent medium amorphous content. |
|   |   |   |   |   |   | 336 | FU-1 major constituent, equal to b (240h). |
| e | 2.6 | 0.05 FU-1 | 900 | SS | 120 | 72 | FU-1 major constituent. |
| f | 2.6 | 0.05 FU-1 | 900 | SS | 104 | 120 | FU-1 medium to major constituent, medium amorphous content. |
|   |   |   |   |   |   | 168 | FU-1 major constituent. |
| g | 1.4 | none | 200 | "Pyrex" | 95 | 672 | amorphous. |
| h | 52 | 0.1 FU-1* | 200 | "Pyrex" | 95 | 264 | medium to major FU-1. |
|   |   |   |   |   |   | 288 | FU-1 major constituent. |

TABLE 16-continued

| Run No. | Scale, g Na AlO₂ | seed, g per g SiO₂ | Agit., rpm | Vessel material | Temp, °C. | Time, h | Product, according to X-ray diffraction |
|---|---|---|---|---|---|---|---|
| | | | | | | 360 | FU-1 major constituent. |

EXAMPLE 21

Other preparations at 95° C.

(a) A KS-300A- based mixture having the composition $$9.64Na_2O.5.4Q_2O.Al_2O_3.59.3SiO_2.3008H_2O$$

containing 0.1 g FU-1 seed per g SiO₂ was made up on the scale of 2.3 g of sodium aluminate and reacted in a "Pyrex"-lined vessel with agitation at 450 rpm at 95° C. for 360 h. The product, after washing thoroughly and drying at 100° C. had the composition $$0.4Na_2O.1.5(TMA)_2O.Al_2O_3.38SiO_2.5.7H_2O$$

and contained FU-1 as its major constituent.

(b) A KS-300A- based mixture having the composition $$3.24Na_2O.5.4Q_2O.Al_2O_3.40SiO_2 1808H_2O$$

and containing 0.1 g FU-1 seed per g SiO₂ was made up on the scale of 2.1 g of sodium aluminate and reacted in a "Pyrex"-lined vessel with agitation at 450 rpm at 95° C. for 360 hours. The product, after washing thoroughly and drying at 100° C. had the composition $$0.25Na_2O.1.4(TMA)_2O.Al_2O_3.33SiO_2.6H_2O$$

and contained FU-1 as its major constituent.

EXAMPLE 22

H-form of FU-1 made at low temperature

The product of run 20h, whose composition after drying at 120° C. overnight was $$1.04Na_2O.1.5Q_2O.Al_2O_3.28SiO_2.8.4H_2O,$$

was exchanged by twice slurrying with 5% HCl (2 ml per g) for 1 hour at 95° C. filtering and washing. It was then dried at 120° C. and calcined at 450° C. for 48 hours in a stream (GHSV 1000) of air saturated with water at 25° C. The calcined product had the composition 0.03Na₂O.Al₂O₃.29 SiO₂ and contained under 0.2% carbon. Table 3 above shows its sorption data.

EXAMPLE 23

Ion-exchanged forms of FU-1

For the following preparations the starting FU-1 was the product of a repeat of Example 1 on the scale of 930 g of sodium aluminate in a 450 liter stainless steel rocking autoclave at 170° C. for 48 hours. Its composition after filtering and washing and overnight drying at 120° C. was $$0.55Na_2O.1.6Q_2O.Al_2O_3.34.7SiO_2.2.9H_2O$$

A. Products of moderate carbon content (i) H-FU-1:

a sample of the above starting FU-1 was twice exchanged by slurrying with 2 ml. 3.65% HCl per g, FU-1 for 1 hour at 90° C., filtering and washing. The washed material was dried overnight at 120° C. A sample of it was calcined at 450° C. for 48 hours in a stream (GHSV 500) of air saturated with water at 25° C. The calcined material contained 0.8% of carbon and had the composition $$0.06Na_2O.Al_2O_3.32.1SiO_2$$

on a carbon-free, water-free basis. Its sorption data are given in Table 3 above.

(ii) RE-H-FU-1:

a sample of calcined material from A(i) was subjected to two successive exchange treatments by slurrying at 90° C. for 1 hour with 3 ml per g FU-1 of 10% rare earth chloride solution of initial pH 3.0, filtering, washing, drying and calcining at 450° C. for 6 hours. The product contained under 0.2% w/w of carbon and had the composition $$0.02Na_2O.0.18(RE)_2O_3.Al_2O_3.31.5SiO_2$$

on a carbon-free, water-free basis. Its sorption data are given in Table 3 above.

(iii) Ca-H-FU-1:

a second portion of calcined H-FU-1 from A(i) was slurry-exchanged for 1 hour at 90° C. with 140 g l⁻¹ CaCl₂ (3 ml per g FU-1), filtered, washed, dried and then calcined at 450° C. in air for 48 hours. The product had the composition (excluding carbon residue 0.6% and hydrogen)

$$0.06Na_2O.0.35CaO.Al_2O_3.34SiO_2$$

i.e. 35% of the theoretical cation sites were filled with calcium ions.

(iv) Ni-H-FU-1:

run A(iii) was repeated using 150 g l⁻¹ Ni(NO₃)₂. The product had the composition $$0.05Na_2O.0.31NiO.Al_2O_3.33SiO_2,$$

excluding carbon residue of 0.5% and hydrogen.

(v) Na-FU-1:by back-exchanging:

run A(iii) was repeated using 140 g l⁻¹ NaCl. The product had the composition $$0.97Na_2O.Al_2O_3.35SiO_2,$$

excluding carbon residue 0.7% and hydrogen. Thus 97% of the theoretical cation sites were filled with Na ions.

(vi) Cu-H-FU-1:

run A(iii) was repeated using a 10% aqueous solution of Cu(NO₃)₂. The product had the composition (excluding 0.3% carbon residue and hydrogen)

0.03Na₂O.0.2CuO.Al₂O₃.33SiO₂.

B. Products of very low carbon content

A sample of exchanged and dried but uncalcined material from A(i), that is, H-TMA-FU-1, was calcined at 450° C. for 24 hours first in flowing ammonia gas (GHSV 500) and then in air saturated with water at 25° C. The product contained no detectable carbon and had the composition (ignoring hydrogen)

0.03Na₂O.Al₂O₃.34SiO₂.

Its sorption data are given in Table 3 above.

EXAMPLE 24

Synthesis with efficient use of TMAOH and silica

The reaction mixture had the composition

3Na₂O.1.5Q₂O.Al₂O₃.25SiO₂.900H₂O and was made by suspending 3430 g of KS300 (composition Na₂O.0.15Al₂O₃.143SiO₂.64H₂O) in a mixture of 2184 g of TMAOH solution and 25 liters of water. Next a solution of 350 g of sodium aluminate and 257.4 g of sodium hydroxide in 5.25 liters of water was stirred in. Finally as seed 170 g of starting FU-1 from example 23 dried and ground to −100 mesh BSS was stirred in. The mixture was reacted in a 44 liter stainless steel autoclave with stirrer speed 400 rpm for 12 hours at 180° C.

The product after filtration, washing and finally drying overnight at 120° C. was major FU-1 with no other phases detected. Its composition was 0.94Na₂O.1.5Q₂O.Al₂O₃.25.5SiO₂.6.4H₂O.

It seems likely that the major cation is Na and that most of the TMA is occluded in the FU-1 lattice. X-ray diffraction data for this sample are shown in Table 17 and FIG. 1.

A sample of this material was converted to the hydrogen form by ion exchange and air-calcination as described in Example 23 A(i). Its composition (excluding carbon residue under 0.2% and hydrogen) was 0.09Na₂O.Al₂O₃.26SiO₂.

Its sorption data are given in Table 3 above. Its X-ray diffraction pattern is shown in Table 17 and FIG. 2.

(b) Run (a) was repeated without seed. The mixture was sampled daily and examined by X-ray diffraction. From 4 to 8 days the solid phase contained FU-1 at a medium to medium-major level, with amorphous material.

EXAMPLE 25

Synthesis with TMA added as chloride

Example 24(a) was repeated on the scale of 8.1 g of sodium aluminate using a mixture of TMA Cl and sodium hydroxide in place of the TMAOH solution, that is, having the composition 9Na⁺.3Q⁺.9OH⁻.3X⁻⁻.Al₂O₃.25SiO₂.900H₂O.

TABLE 17

| | Na - TMA form | | | H - form, air - calcined | | |
|---|---|---|---|---|---|---|
| °2θ | d, A | | Relative Intensity | °2θ | d, A | Relative Intensity |
| *5.4 | 16 | ⎫⎫ | ~7 | *5.5 | 16 | ⎫⎫ ~12 |
| *6.1 | 14.5 | ⎭⎭ | ~7 | *6.2 | 14.3 | ⎭⎭ ~7 |
| 9.16 | 9.65 | ⎫⎫ | 50 | 7.75 | 11.4 | ⎫ ~4 |
| 10.7 | 8.3 | ⎭⎭ | ~3 | 9.60 | 9.21 | ⎫ 56 |
| 12.80 | 6.92 | ⎫⎫ | 27 | 11.06 | 8.0 | ⎭ 6 |
| 13.4 | 6.6 | ⎭⎭ | ~2 | 12.93 | 6.85 | ⎫ 63 |
| 14.96 | 5.92 | ⎫⎫ | 2 | 13.51 | 6.6 | ⎭ ~5 |
| 15.40 | 5.75 | ⎭⎭ | 2 | 15.11 | 5.86 | ⎫ 3 |
| 16.88 | 5.25 | ⎫ | 15 | 15.61 | 5.68 | ⎭ 2 |
| 17.5 | 5.1 | | ~2 | 17.08 | 5.19 | 3 |
| 19.26 | 4.61 | | 50 | 19.57 | 4.54 | ⎫ 46 |
| 20.7 | 4.3 | | ~2 | ~21.0 | 4.2 | ⎭ ~2 |
| 21.80 | 4.08 | | ~11 | 21.90 | 4.06 | ~15 |
| 23.77 | 3.74 | | ~23 | 23.99 | 3.71 | ~24 |
| 24.15 | 3.68₅ | | ~17 | 24.40 | 3.65 | ~23 |
| 25.97 | 3.43 | | 100 | 26.21 | 3.40 | 100 |
| 27.48 | 3.25 | | ~4 | 27.93 | 3.20 | ~3 |
| 28.40 | 3.14 | | ~2 | 28.63 | 3.12 | ~2 |
| 30.53 | 2.93 | | 6 | 29.53 | 3.02₅ | ~5 |
| 33.63 | 2.66₅ | ⎫ | 2 | 31.06 | 2.88 | 11 |
| 34.08 | 2.63 | ⎭ | 2 | 33.91 | 2.64 | ⎫ ~2 |
| 35.48 | 2.53 | | ~2 | 34.41 | 2.61 | ⎭ ~2 |
| 36.38 | 2.47 | ⎫⎫ | ~2 | 35.53 | 2.53 | ⎫ ~2 |
| 37.30 | 2.41 | ⎭⎭ | ~3 | 36.63 | 2.45 | ⎫ ~2 |
| 43.23 | 2.09 | ⎫ | ~2 | 37.16 | 2.42 | ⎭ ~2 |
| 44.78 | 2.02₅ | ⎭ | 6 | 37.91 | 2.37 | ⎫⎫ ~3 |
| 48.66 | 1.871 | ⎫ | 9 | 43.49 | 2.08 | ⎭⎭ 2 |
| 49.53 | 1.840 | | 6 | 45.24 | 2.00 | 5 |
| 50.41 | 1.810 | | ~2 | 47.29 | 1.92 | 2 |
| 51.22 | 1.783 | | 4 | 49.06 | 1.857 | ⎫ 8 |
| 52.87 | 1.732 | ⎭ | ~2 | 49.96 | 1.826 | ⎭ 5 |
| | | | | 50.89 | 1.794 | 3 |
| | | | | 52.04 | 1.757 | ⎫ 3 |
| | | | | 53.29 | 1.719 | ⎭ 2 |

Symbols in Table:
) lines not completely resolved
)) lines not resolved
~approximate Relative Intensity (because of interference from adjacent lines)
*these lines may be due to scatter The seed used was Example 24 (a) product. The solid phase formed was FU-1 was no other detectable phase.

EXAMPLE 26

Potassium-containing synthesis mixture

A mixture having the composition 9.0K₂O.0.6Na₂O.5.4Q₂O.Al₂O₃.59.3SiO₂.3008H₂O was made up on the scale of 1.53 g of alumina (equivalent to 2.7 g sodium aluminate) using a solution of pure alumina in potassium hydroxide as the source of alumina. The silica source was KS300, which contributed the 0.6 mol of Na₂O. The mixture was reacted in a stainless steel autoclave without inert gas and with moderate agitation (900 rpm) at 180° C. for 2 days. The solid phase was collected on a filter, washed and dried and examined by X-ray diffraction. It was FU-1 of high purity.

A corresponding mixture using sodium aluminate (compare Example 9c) was found to produce high purity FU-1 in 17 hours in otherwise equal conditions.

What is claimed is:

1. A process which comprises contacting an alkylbenzene or mixture of alkylbenzenes under isomerisation conditions in the vapour or liquid phase with a catalyst comprising FU-1.

2. A process according to claim 1 in which the reactants are present in the vapour phase, added free hydrogen is substantially absent, the temperature is in the range 200° to 450° C., the pressure is in the range 1 to 5 atm. abs. and the catalyst contains no hydrogenation/dehydrogenation component.

3. A process according to claim 1 in which the alkylbenzenes are present in the liquid phase, added free hydrogen is substantially absent, the temperature is in the range 0° to 350° C., the pressure is in the range 5 to 70 atm. abs. and the catalyst contains no hydrogenation/dehydrogenation component.

4. A process according to claim 1 in which isomerisation is in the vapour phase, is conducted in the res ce of hydrogen and the FU-1 contains a hydrogenation/dehydrogenation component.

5. A process according to claim 1 in which the reaction mixture contains at least one of (a) water vapour in a concentration of 500 to 10000 ppm w/w and (b) an alicyclic hydrocarbon and (e) an alkane having 2 to 10 carbon atoms in the molecule.

* * * * *